(12) United States Patent
Geffen et al.

(10) Patent No.: US 11,883,006 B2
(45) Date of Patent: Jan. 30, 2024

(54) ARTICULATION ARM LINK

(71) Applicant: VALUEBIOTECH ISRAEL LTD., Ness Ziona (IL)

(72) Inventors: Nir Geffen, Ramat HaSharon (IL); Avraham Rami Lore, Kiryat Tivon (IL); Eldar Cohen, Yokneam Elite (IL); Alexander Mikler, Rehovot (IL); Paul Price, Nes Tziona (IL); Antonello Forgione, Milan (IT); Renzo Zaltieri, Milan (IT)

(73) Assignee: VALUEBIOTECH ISRAEL LTD., Ness Ziona (IL)

( * ) Notice: Subject to any disclaimer, the term of this patent is extended or adjusted under 35 U.S.C. 154(b) by 571 days.

(21) Appl. No.: 16/972,101

(22) PCT Filed: Jun. 4, 2019

(86) PCT No.: PCT/IB2019/054636
§ 371 (c)(1),
(2) Date: Dec. 4, 2020

(87) PCT Pub. No.: WO2019/234626
PCT Pub. Date: Dec. 12, 2019

(65) Prior Publication Data
US 2021/0219820 A1 Jul. 22, 2021

(30) Foreign Application Priority Data

Jun. 4, 2018 (IL) .......................................... 259807

(51) Int. Cl.
*A61B 1/00* (2006.01)
*A61B 1/005* (2006.01)
(Continued)

(52) U.S. Cl.
CPC ............ *A61B 1/0055* (2013.01); *A61B 90/50* (2016.02); *B25J 9/06* (2013.01)

(58) Field of Classification Search
CPC ....... A61B 1/0055; A61B 90/50; A61B 34/30; A61B 2034/306; B25J 9/06; B25J 18/00
See application file for complete search history.

(56) References Cited

U.S. PATENT DOCUMENTS

| 5,888,200 A | 3/1999 | Walen |
| 2003/0036748 A1 | 2/2003 | Cooper et al. |

(Continued)

FOREIGN PATENT DOCUMENTS

| EP | 2249690 A1 | 11/2010 |
| EP | 2755805 A2 | 7/2014 |

(Continued)

OTHER PUBLICATIONS

International Search Report and Written Opinion for PCT/IB2019/054636, dated Sep. 23, 2019.

(Continued)

*Primary Examiner* — Victor L MacArthur
(74) *Attorney, Agent, or Firm* — Merchant & Gould P.C.

(57) ABSTRACT

A link for an articulation arm includes a vertebra, two outer bearing portions, two inner bearing portions and four control bore holes. The vertebra has a first base and a second base. The two outer bearing portions are formed on the first base and are located on a radial line of the first base. The two inner bearing portions are formed on the second base and are located on a radial line of the second base. The two of the four control bore holes enter the second base and exit a respective one of the outer bearing portions. The other two of the control bore holes enter the first base and exit a respective one of the inner bearing portions.

11 Claims, 19 Drawing Sheets

(51) Int. Cl.
   *A61B 90/50*    (2016.01)
   *B25J 9/06*     (2006.01)

(56) References Cited

U.S. PATENT DOCUMENTS

| | | |
|---|---|---|
| 2003/0135204 A1 | 7/2003 | Lee et al. |
| 2004/0138529 A1 | 7/2004 | Wiltshire et al. |
| 2009/0099420 A1 | 4/2009 | Woodley et al. |
| 2010/0116081 A1 | 5/2010 | Pistor et al. |
| 2012/0165608 A1 | 6/2012 | Banik et al. |
| 2017/0000315 A1* | 1/2017 | Pistor ................. B25J 9/104 |

FOREIGN PATENT DOCUMENTS

| | | |
|---|---|---|
| WO | 2012/128591 A2 | 9/2012 |
| WO | 2013/009699 A2 | 1/2013 |

OTHER PUBLICATIONS

Communication pursuant to Rules 70(2) and 70a(2) EPC for European Patent Application 19814138.4. (dated Apr. 12, 2022).
Search Report for European Application No. 19814138.4. (dated Mar. 23, 2022).

* cited by examiner

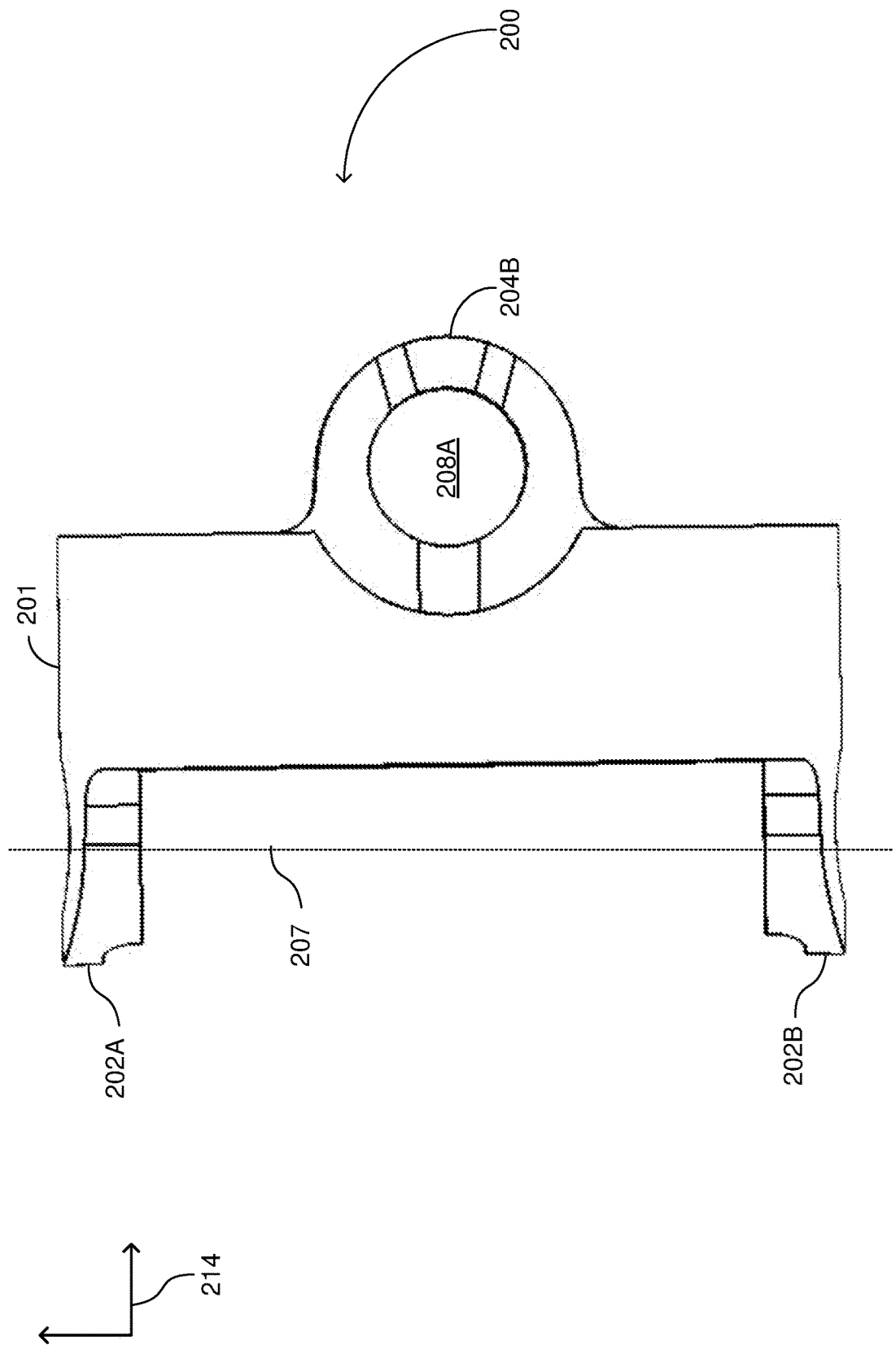

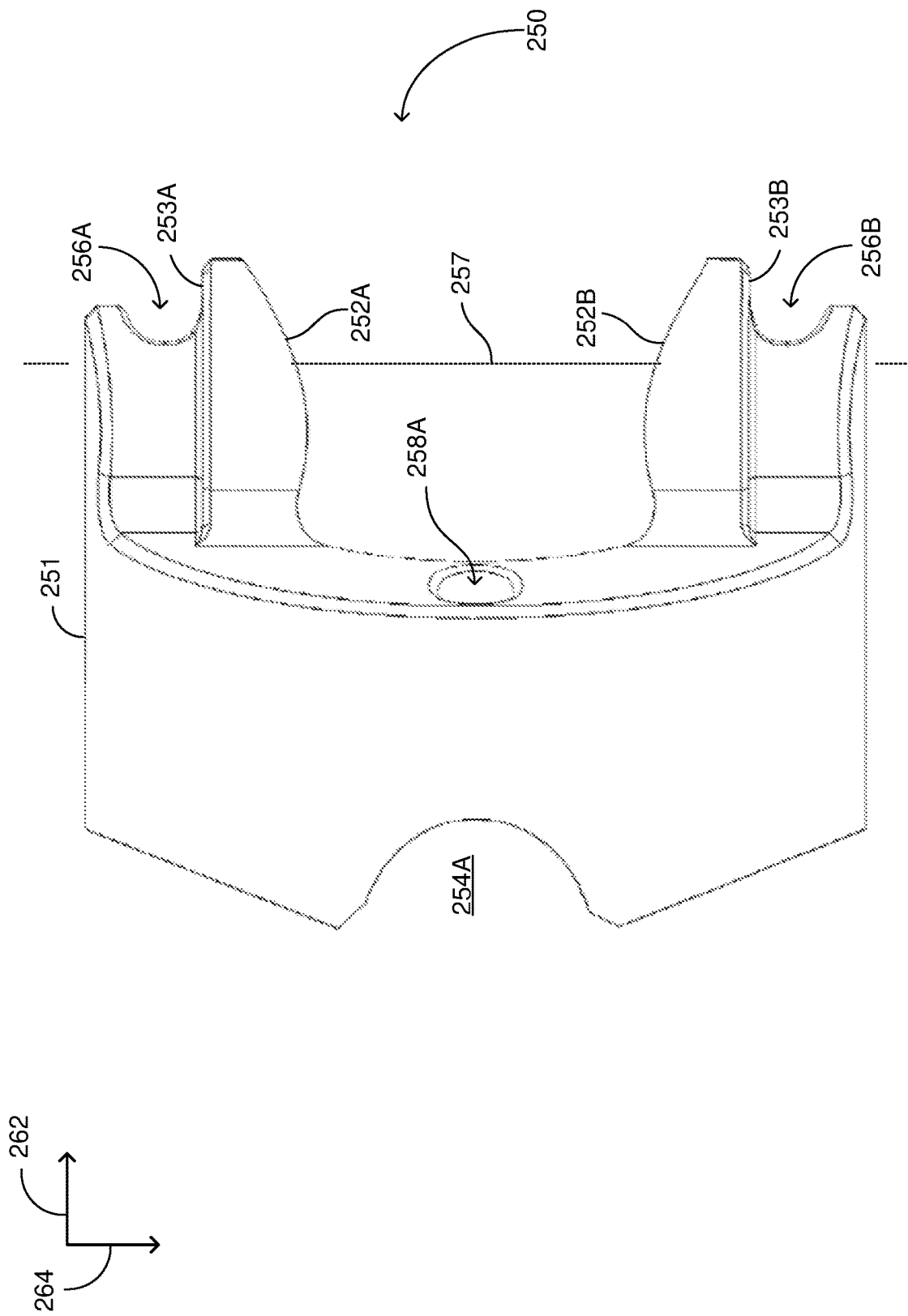

ARTICULATION ARM LINK

This application is a National Stage application of PCT/IB2019/054636, filed Jun. 4, 2019, which claims priority to Israeli Patent Application No. 259807, filed Jun. 4, 2018, which applications are incorporated herein by reference. To the extent appropriate, a claim of priority is made to each of the above-disclosed applications.

FIELD OF THE DISCLOSED TECHNIQUE

The disclosed technique relates to articulation arms in general, and to articulation arms links, in particular.

BACKGROUND OF THE DISCLOSED TECHNIQUE

Articulation arms are known in the art and are generally employed for controlling the direction in which a tool or object are pointing. Also known in the art is employing articulation arms when performing various medical procedures, to control the tool or tools attached to the articulation arm. Articulation arms are typically composed of links, which are rotatable one with respect to the other and are typically controlled by controlling the tension of cables passing through the links.

U.S. Patent Application Publication 2003/0135204 to Lee eat al, entitled "Robotically Controlled Medical Instrument with Flexible Section", directs to a flexible articulation arm which includes a plurality of ribs. The ribs are connected therebetween by ridges. The ridges are arranged at 90 degrees to each other. Cables pass through holes in the ridges.

U.S. Patent Application Publication 2009/0099420 to Woodley et al, entitled "System for Managing Bowden Cables in Articulating Instruments", directs to a vertebrae-type control ring having two pairs of joints or hinges. The first pair projecting perpendicularly from a first face of the vertebra. The second pair, located 90 degrees from the first pair, projecting perpendicularly away from an opposite face of the vertebra. Four holes pass through the edge of vertebra-type control ring that may act as attachment sites or throughway for cables.

SUMMARY OF THE PRESENT DISCLOSED TECHNIQUE

It is an object of the disclosed technique to provide a novel link for an articulation arm. In accordance with the disclosed technique, there is thus provided a link for an articulation arm, which includes a vertebra, two outer bearing portions, two inner bearing portions and four control bore holes. The vertebra has a first base and a second base. The two outer bearing portions are formed on the first base and are located on a radial line of the first base. The two inner bearing portions are formed on the second base and are located on a radial line of the second base. The two of the four control bore holes enter the second base and exit a respective one of the outer bearing portions. The other two of the control bore holes enter the first base and exit a respective one of the inner bearing portions.

In accordance with another aspect of the disclosed technique, there is thus provided an articulation arm including a plurality of links. Each link includes a vertebra, two outer bearing portions, two inner bearing portions and four control bore holes. The vertebra has a first base and a second base. The two outer bearing portions are formed on the first base and are located on a radial line of the first base. The two inner bearing portions are formed on the second base and are located on a radial line of the second base. The two of the four control bore holes enter the second base and exit a respective one of the outer bearing portions. The other two of the control bore holes enter the first base and exit a respective one of the inner bearing portions. The outer bearing portions of one link are inserted into the inner bearing portions of an adjacent link, creating a bearing such that two adjacent links can rotate one with respect to the other.

BRIEF DESCRIPTION OF THE DRAWINGS

The disclosed technique will be understood and appreciated more fully from the following detailed description taken in conjunction with the drawings in which:

FIGS. 3A-3F are schematic illustrations of a link for an articulation arm constructed and operative in accordance with a further embodiment of the disclosed technique;

FIGS. 4A-4E are schematic illustrations of a link for an articulation arm, constructed and operative in accordance with another embodiment of the disclosed technique.

DETAILED DESCRIPTION OF THE EMBODIMENTS

Figure 1A:
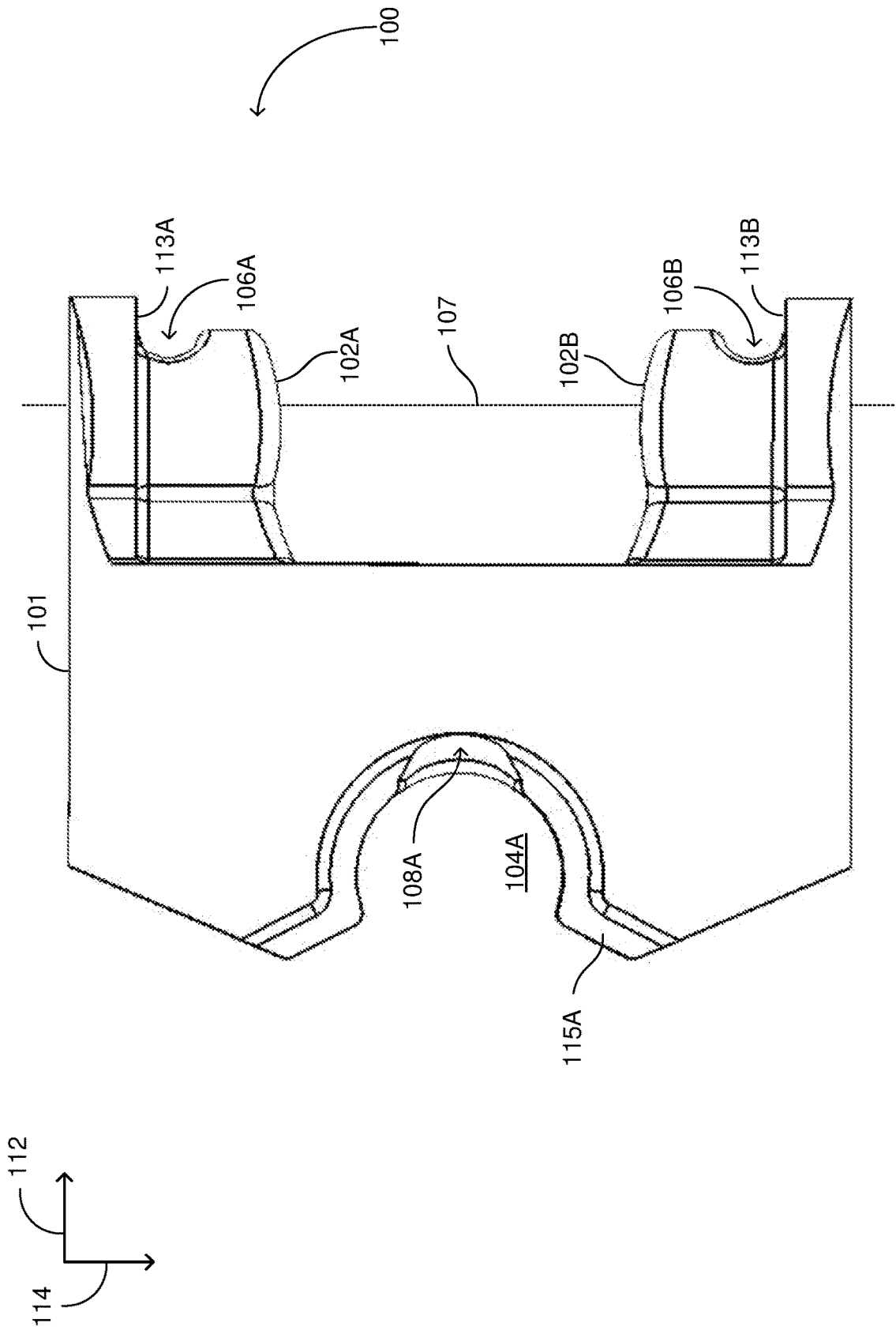
FIGS. 1A-1E are schematic illustrations of a link for an articulation arm, constructed and operative in accordance with an embodiment of the disclosed technique.
Figure 1B:
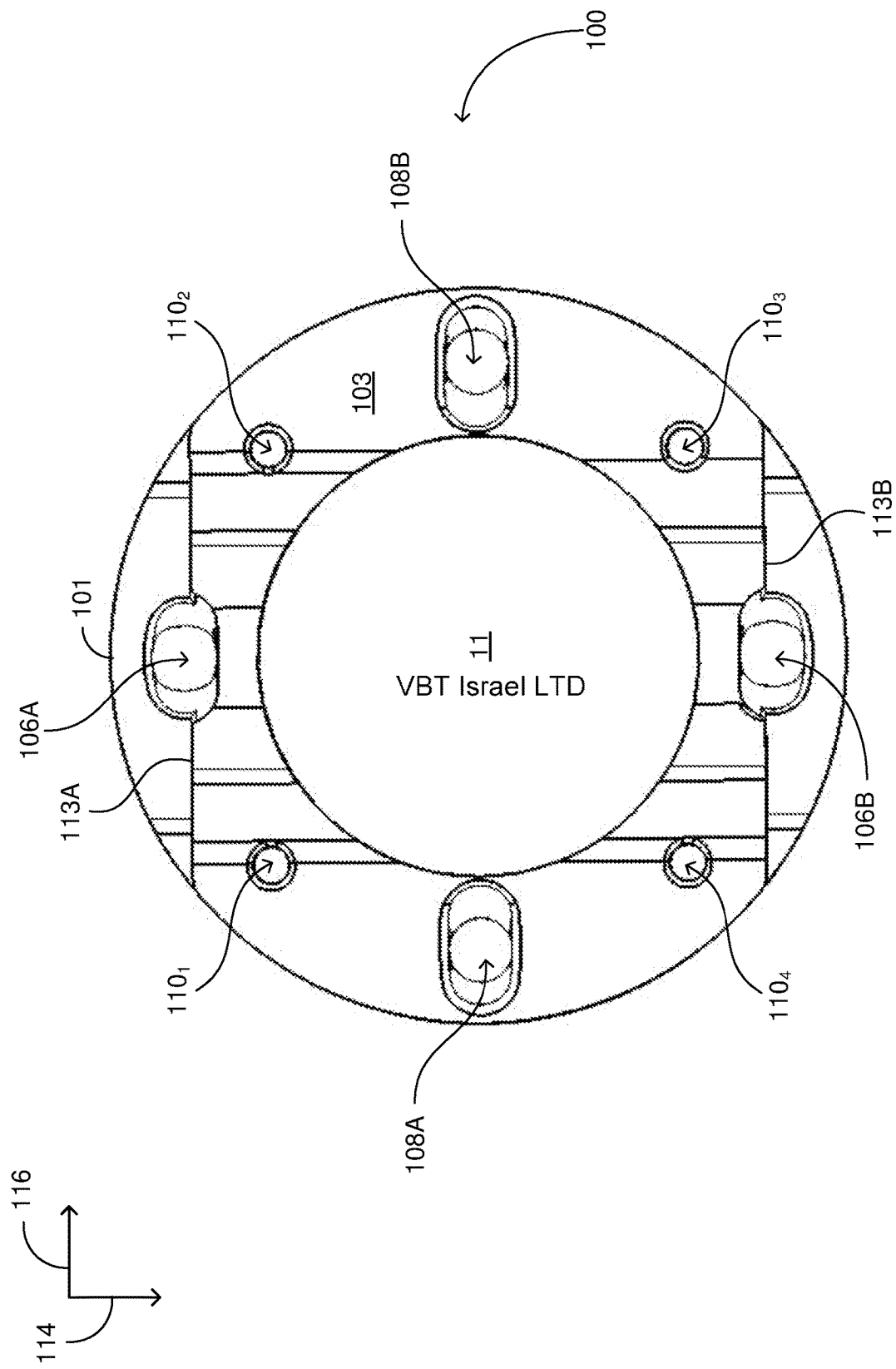
Figure 1C:
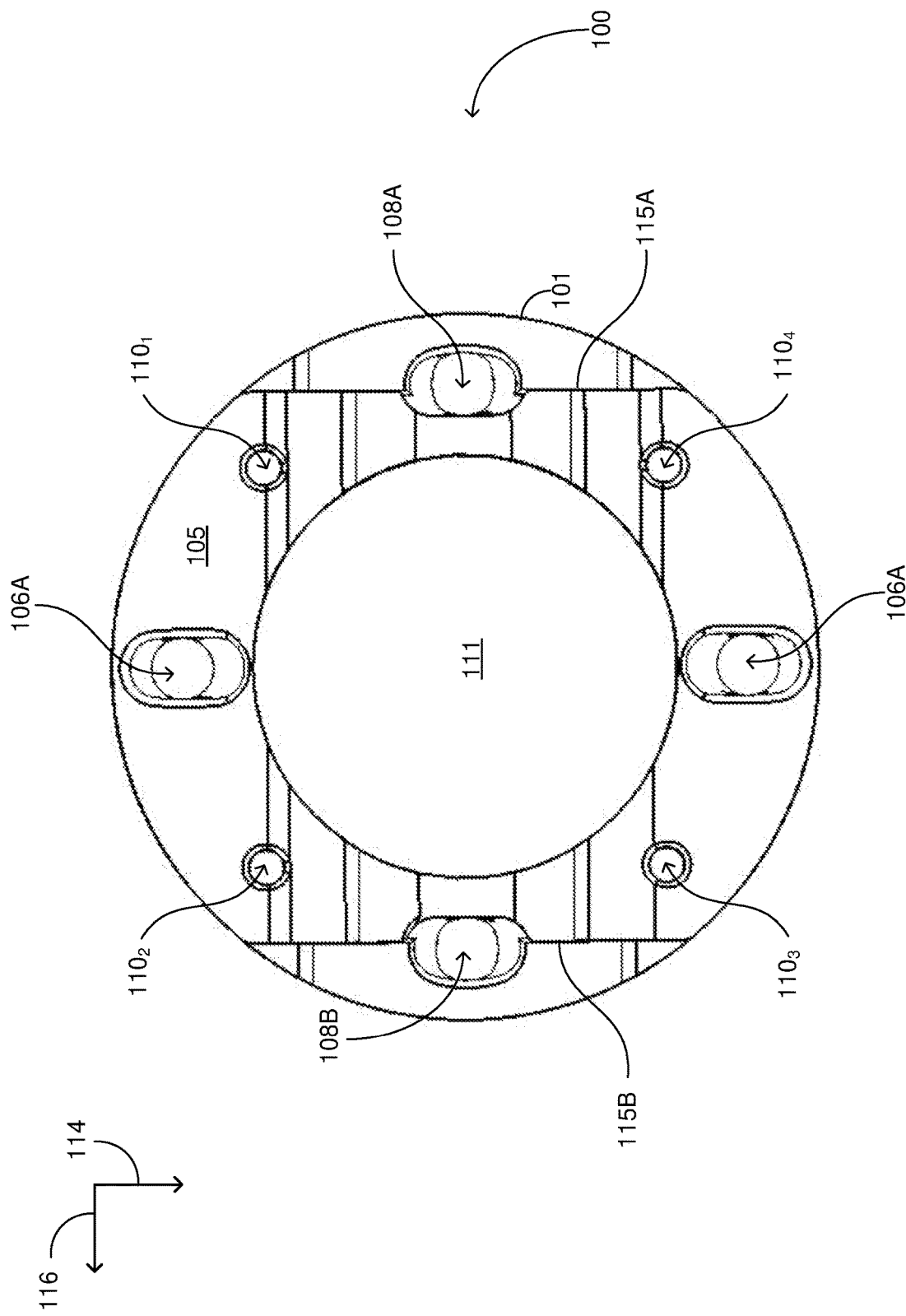
Figure 1D:
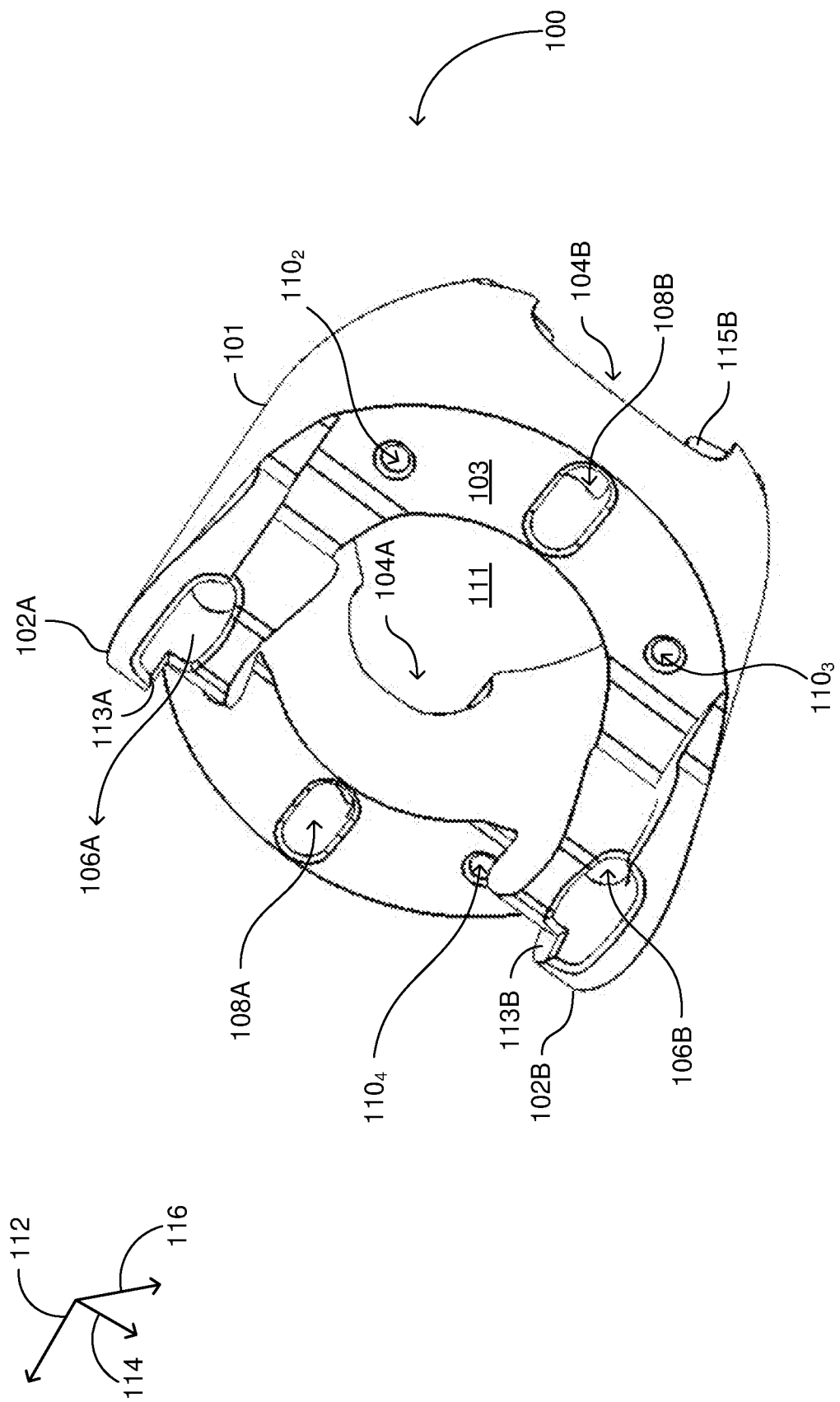
Figure 1E:
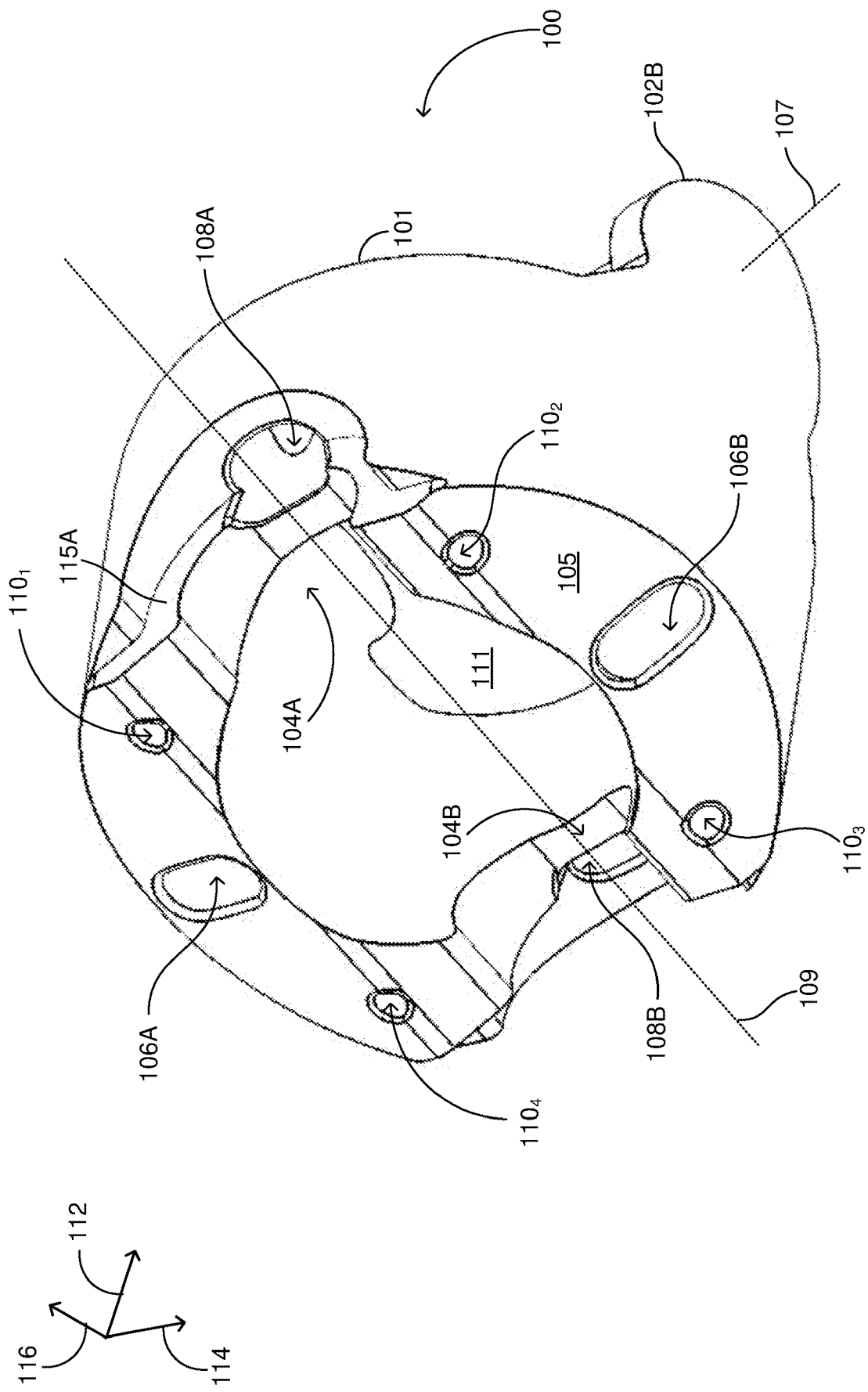

The disclosed technique overcomes the disadvantages of the prior art by providing a novel link for an articulation arm. The link includes a cylindrical vertebra, two outer bearing portions, and two inner bearing portions. The cylindrical vertebra includes a first base and a second base. The two outer bearing portions are formed on a radial line (i.e., a line which intersects the axis of the cylinder and is also perpendicular to the axis of the cylinder) on the first base. The two inner bearing portions, formed on a radial line on the second base. The link includes four control bore holes for control cables or wires to pass there through referred to herein as 'control bore holes'. Control cable or wires are employed for controlling the curvature the articulation arm and consequently the direction to which the distal end of the articulation arm, points. According to the disclosed technique, two of the control bore holes enter the second base and exit a respective one of the outer bearing portions. The other two of the control bore holes enter the first base and exit a respective one of the inner bearing portions. Consequently, the area available for utility bore holes increases. Herein, 'utility bore holes' refer to bore holes through which cable or wires employed for operating a device pass. The device is located at the distal end of the articulation arm. The cables operating the device are for example, electric cable operative to provide electric power to the device or for transmitting a signal or signals to or from the device. The utility cables may also be optic cables operating to deliver light to or from the device.

Reference is now made to FIGS. 1A-1E, which are schematic illustrations of a link for an articulation arm, generally referenced 100, constructed and operative in accordance with an embodiment of the disclosed technique. Link 100 includes a cylindrical vertebra 101 which includes two bases, a first base 103 and a second base 105. Two outer bearing portions 102A and 102B are formed on first base 103 and are located on a radial line 107 of first base 103. In FIGS. 1A-1E, two outer bearing portions 102A and 102B are two axial shoulders 102A and 102B protruding from one base of the cylinder. Two inner bearing portions 104A and 104B are formed in second base 105 and are located on a radial line 109 of second base 105. Radial line 109 is perpendicular to radial line 107. In FIGS. 1A-1E, two inner bearing portions 104A and 104B are two axial recesses 104A and 104B. Link 100 further includes and a central bore 111. Each of axial shoulders 102A and 102B includes a respective ledge 113A and 113B. Each of axial recesses 104A and 104B includes a respective ledge 115A and 115B.

Link 100 includes four control bore holes 106A, 106B, 108A and 108B. Two of the control bore holes 106A and 106B enter second base 105 and exit a respective one of the outer bearing portions 102A and 102B. The other two of the control bore holes 108A and 108B enter first base 103 and exit a respective one of the inner bearing portions 104A and 104B. Each of control bore holes 106A, 106B, 108A and 108B widens at the exits thereof to enable rotational motion of the link 100 when a control cable passes through control bore holes 106A, 106B, 108A and 108B Link 100 further include at least one utility bore hole. In FIGS. 1A-1F, four utility bore holes 110$_1$, 110$_2$, 110$_3$ and 110$_4$ are depicted as an example. Utility bore holes 110$_1$, 110$_2$, 110$_3$ and 110$_4$ pass through link 100 in the longitudinal direction 112 thereof.

Figure 2:
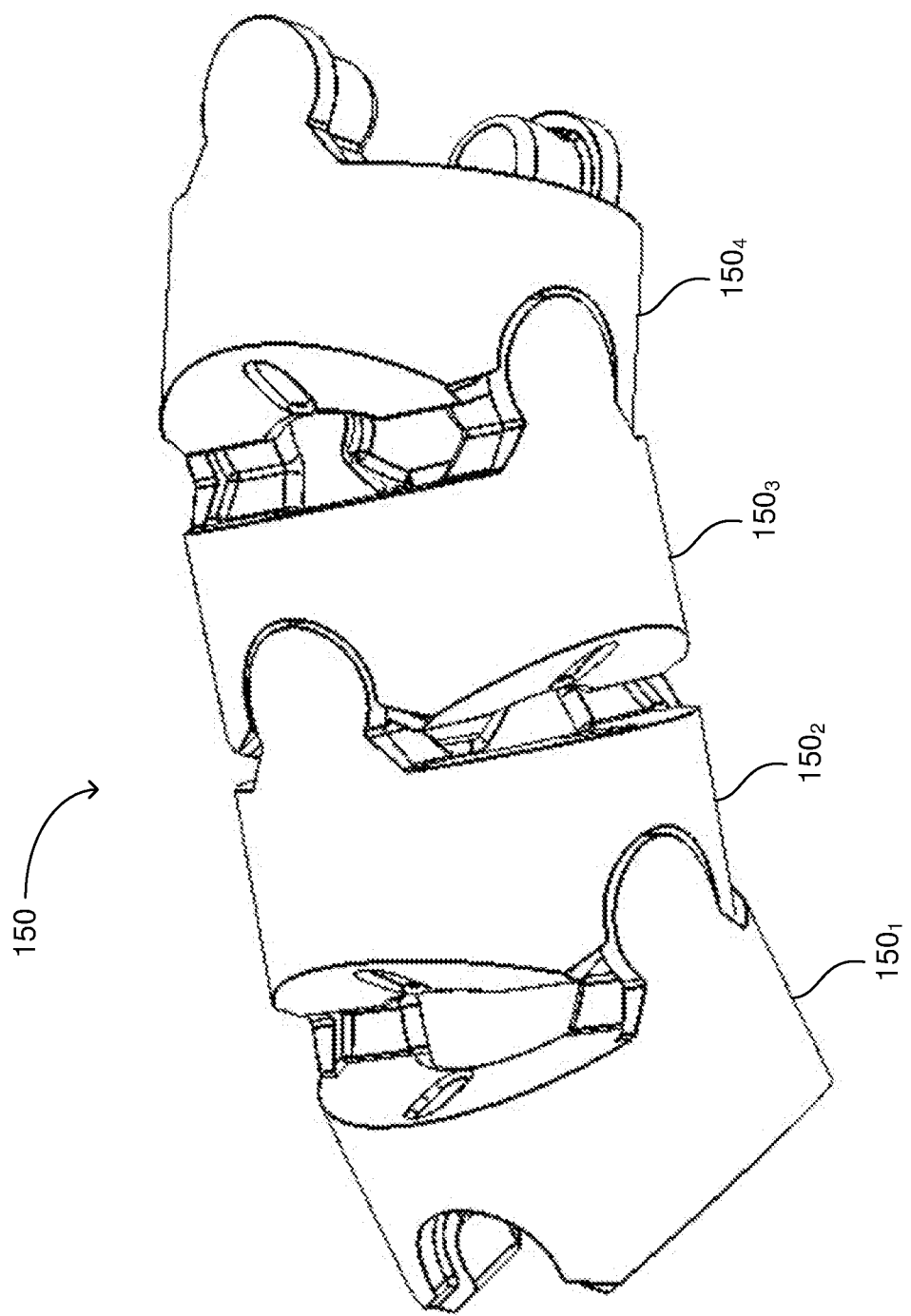
FIG. 2 is a schematic illustration of an exemplary articulation arm, constructed and operative in accordance with another embodiment of the disclosed technique.

Two links connect with each other by connecting the outer bearing portions of one link with the inner bearing portions of another link. Two links such as link 100 connect inserting the axial shoulders of one link to the axial recesses of the other link, thereby creating a bearing about which the two links rotate one with respect to the other. The ledges of the axial shoulders, such as ledges 113A, 113B are aligned with ledges 115A and 115B of the axial recesses, thereby preventing the two links from moving one with respect to the other in either one of the lateral directions 114 and 116. As mentioned above when the control bore holes pass through the bearings of the links, the area available for utility bore holes increases. Reference is now made to FIG. 2, which is a schematic illustration of an exemplary articulation arm, generally referenced 150, constructed and operative in accordance with another embodiment of the disclosed technique. Articulation arm 150 includes four links 150$_1$, 150$_2$, 150$_3$ and 150$_4$. Each one of links 150$_1$, 150$_2$, 150$_3$ and 150$_4$ is similar to link 100 (FIGS. 1A-1F). As depicted in FIG. 2, the axial shoulders of link 150$_1$ are inserted into the axial recess of link 150$_2$ creating a bearing between link 150$_1$ and link 150$_2$ such that link 150$_1$ and link 150$_2$ rotate one with respect to the other. Similarly, the axial shoulders of link 150$_2$ are inserted into the axial recess of link 150$_3$ creating a bearing between link 150$_2$ and link 150$_3$ such that link 150$_2$ and link 150$_3$ rotate one with respect to the other. Also, the axial shoulders of link 150$_3$ are inserted into the axial recess of link 150$_4$ creating a bearing between link 150$_3$ and link 150$_4$ such that link 150$_3$ and link 150$_4$ rotate one with respect to the other. Since, the axial shoulders and the axial recesses are located on perpendicular radial lines, the axis of rotation between link 150$_1$ and link 150$_2$ is perpendicular to the axis of rotation between link 150$_2$ and link 150$_3$. Similarly, the axis of rotation between link 150$_2$ and link 150$_3$ is perpendicular to the axis of rotation between link 150$_3$ and link 150$_4$. In general, two adjacent axis of rotations, between pair of links, are perpendicular one with respect to the other.

Figure 3B:
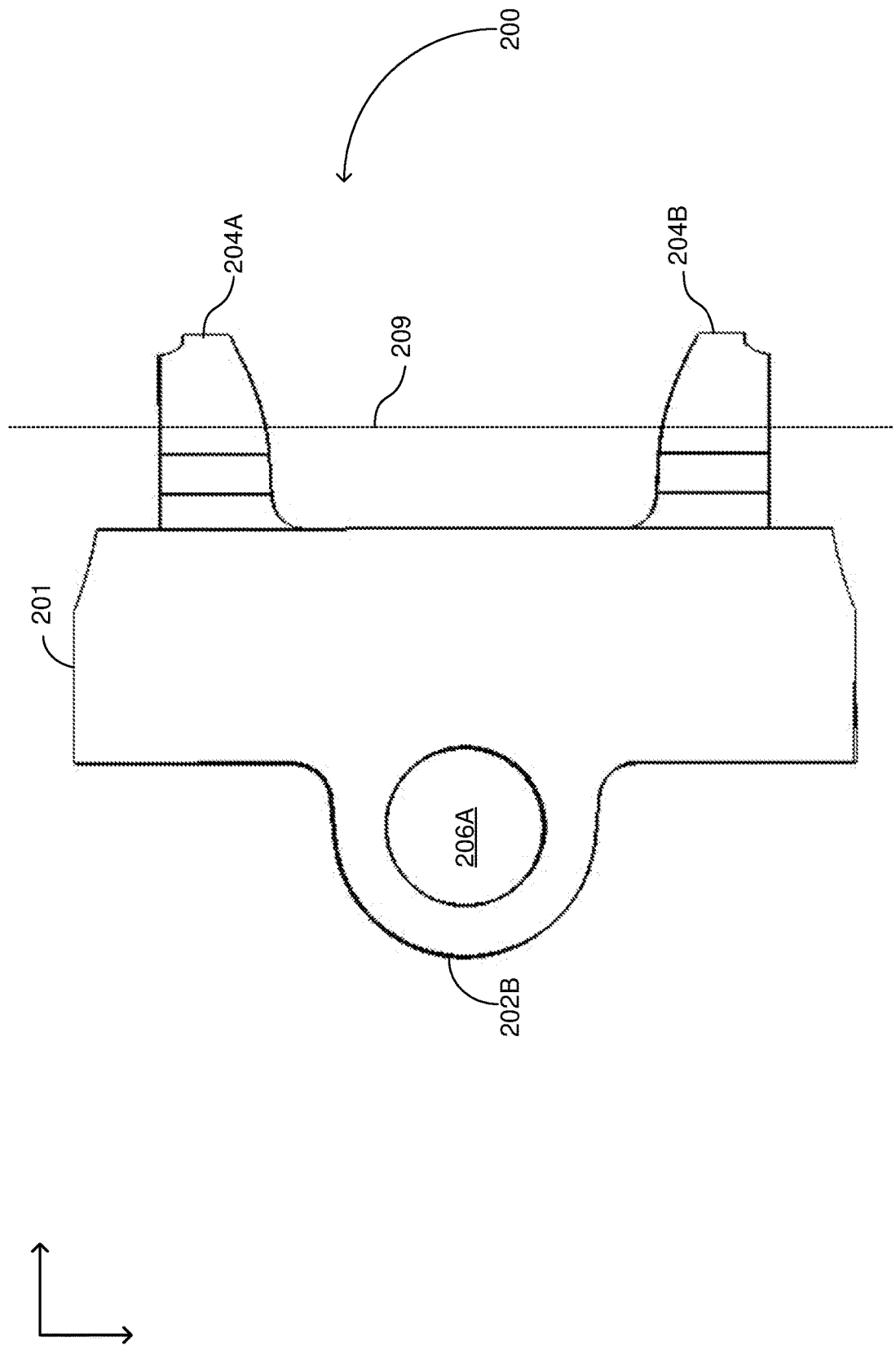
Figure 3C:
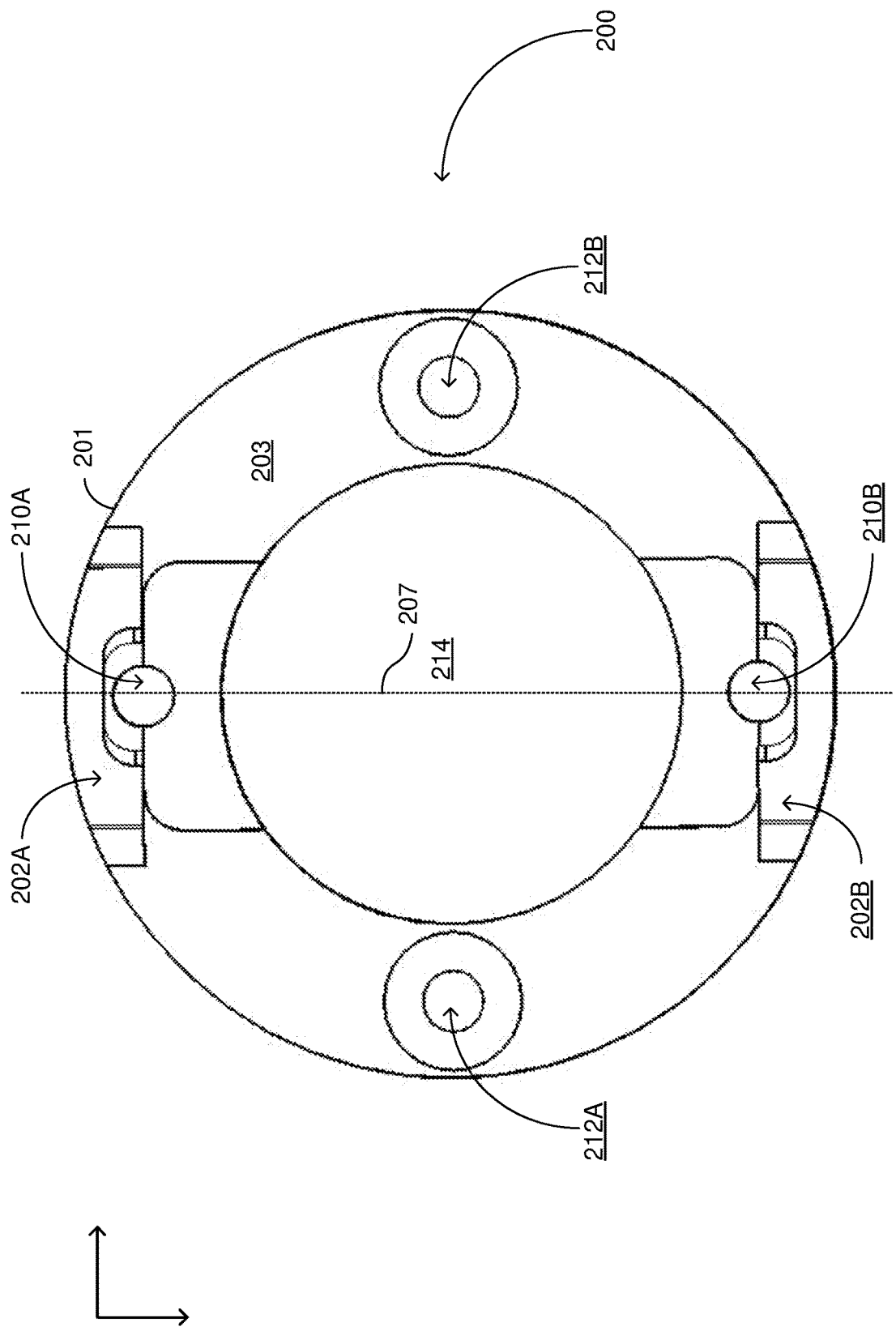
Figure 3D:
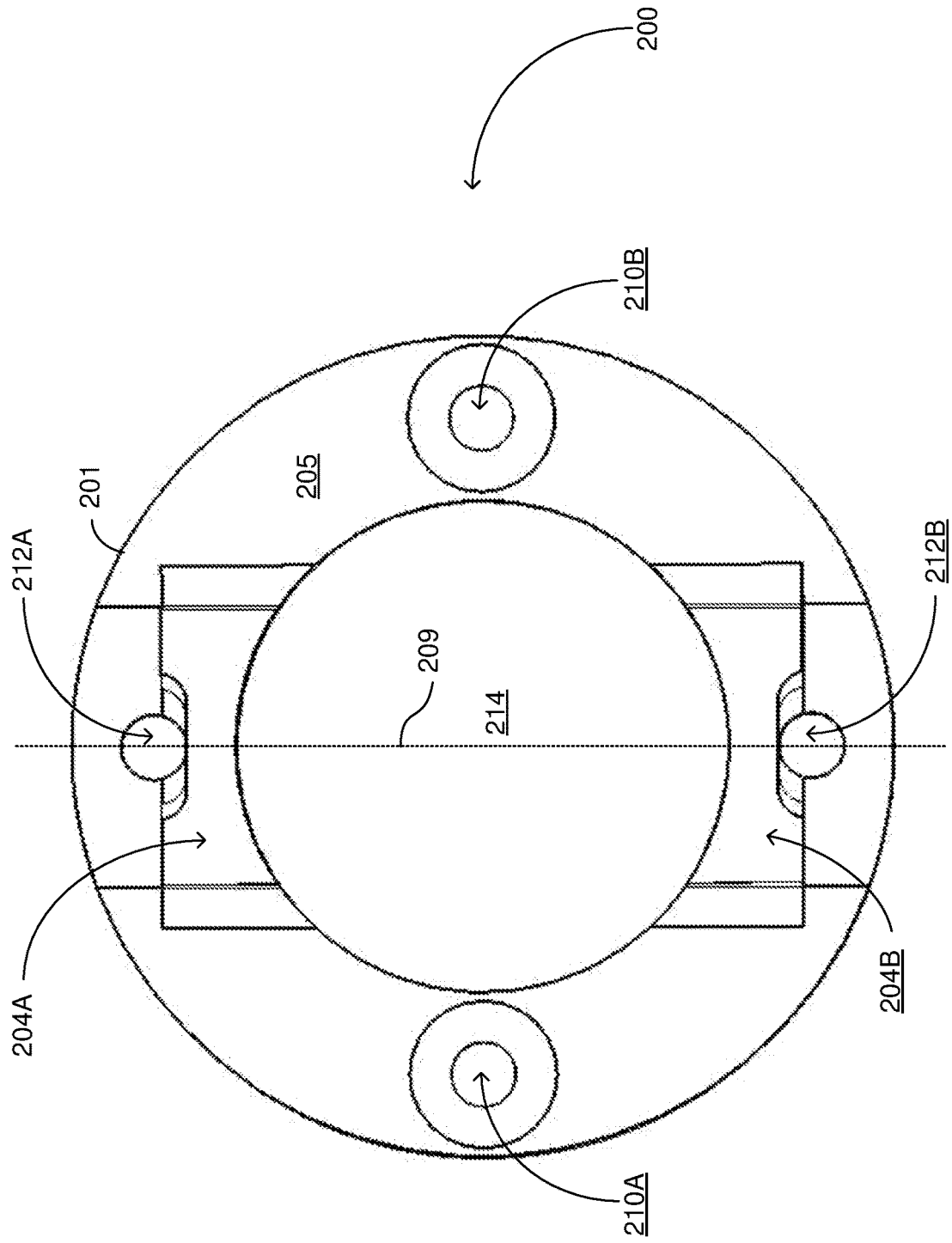
Figure 3E:
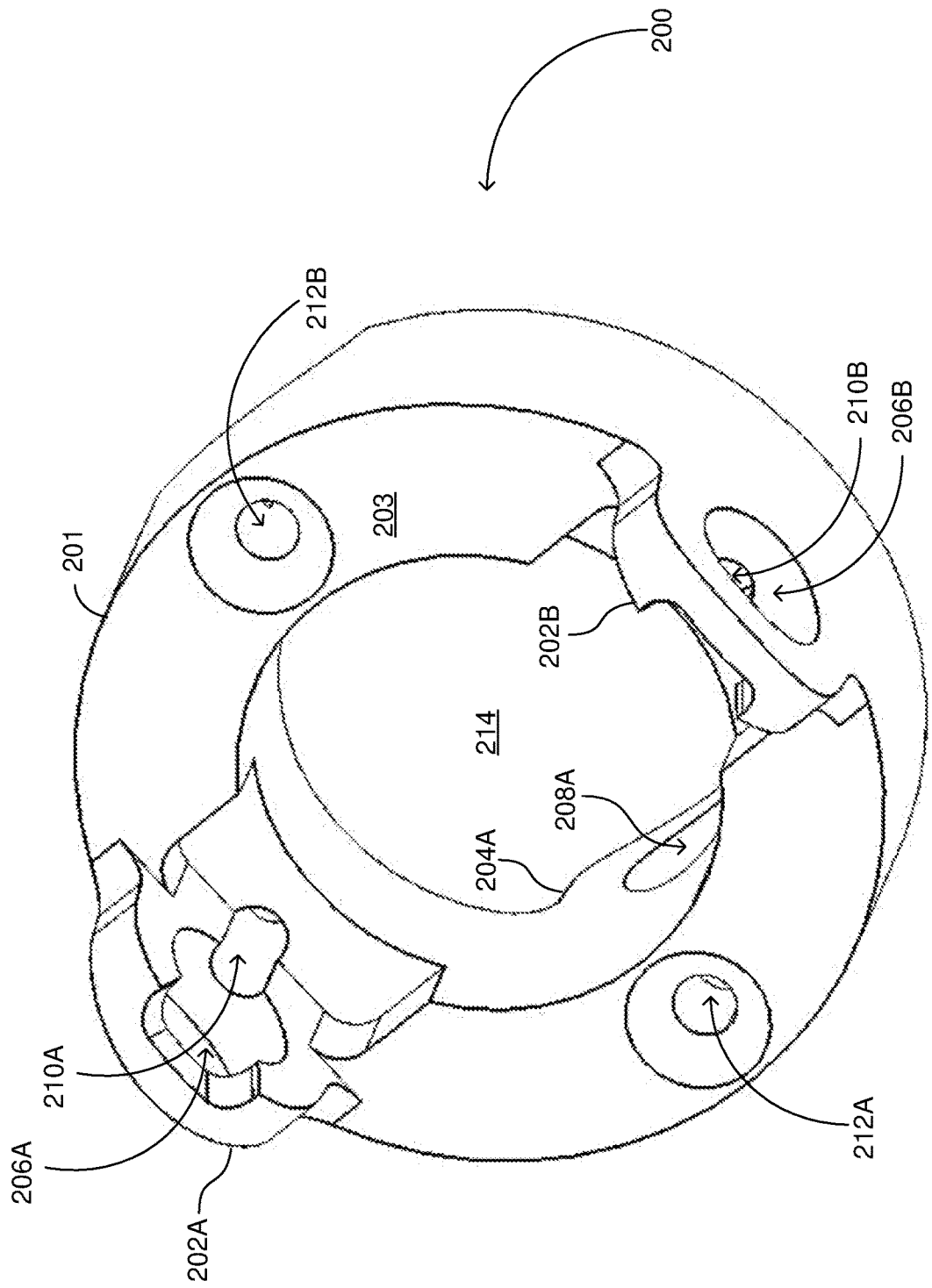
Figure 3F:
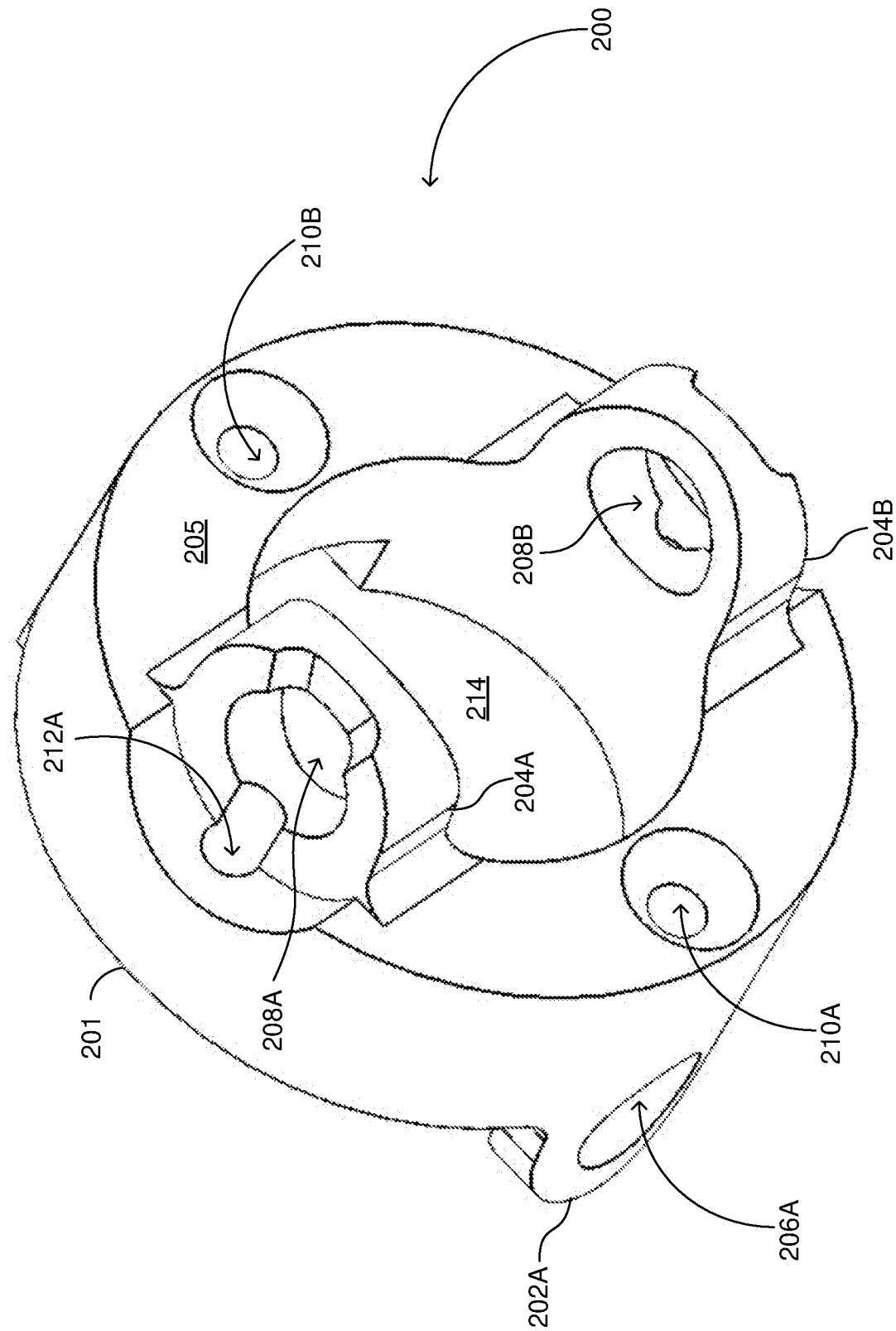
Figure 3G:
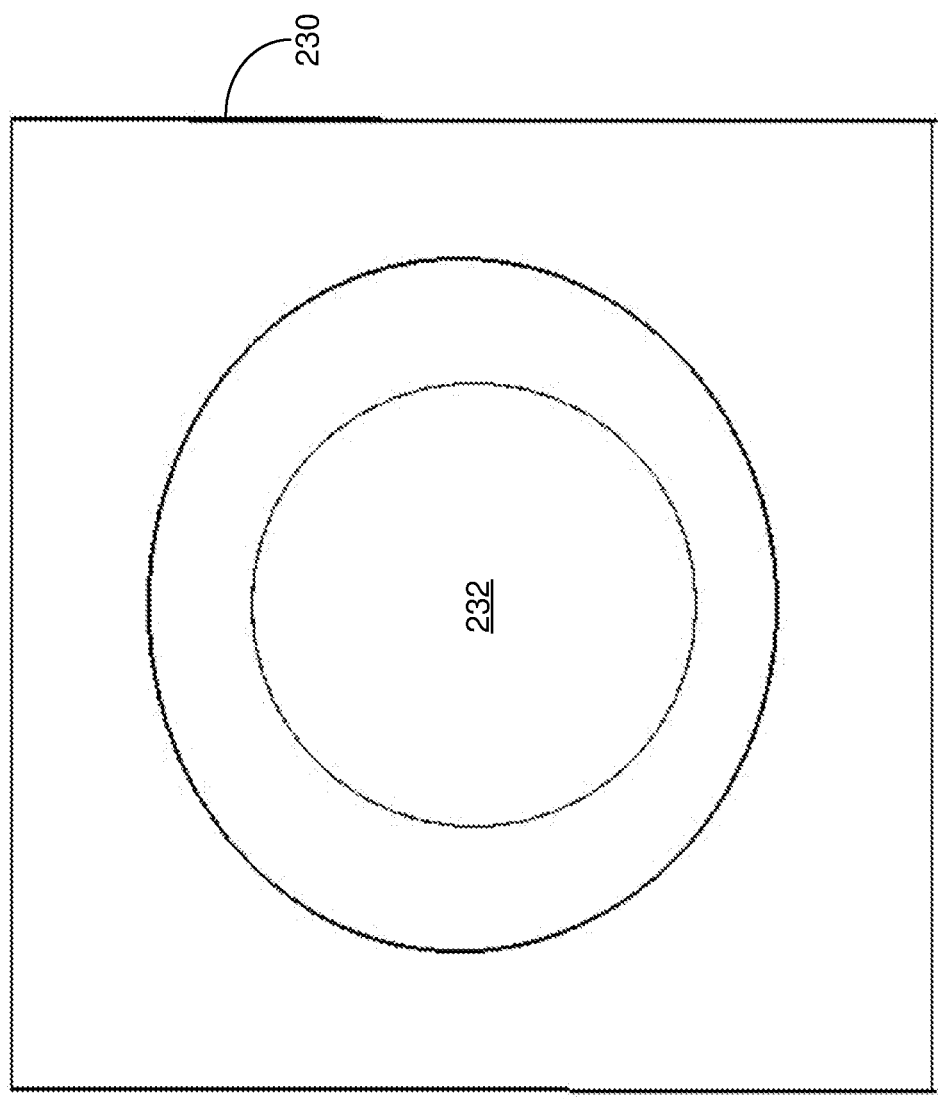
FIGS. 3G and 3H are schematic illustration of a pin for connecting two links, constructed and operative in accordance with a further embodiment of the disclosed technique.
Figure 3H:
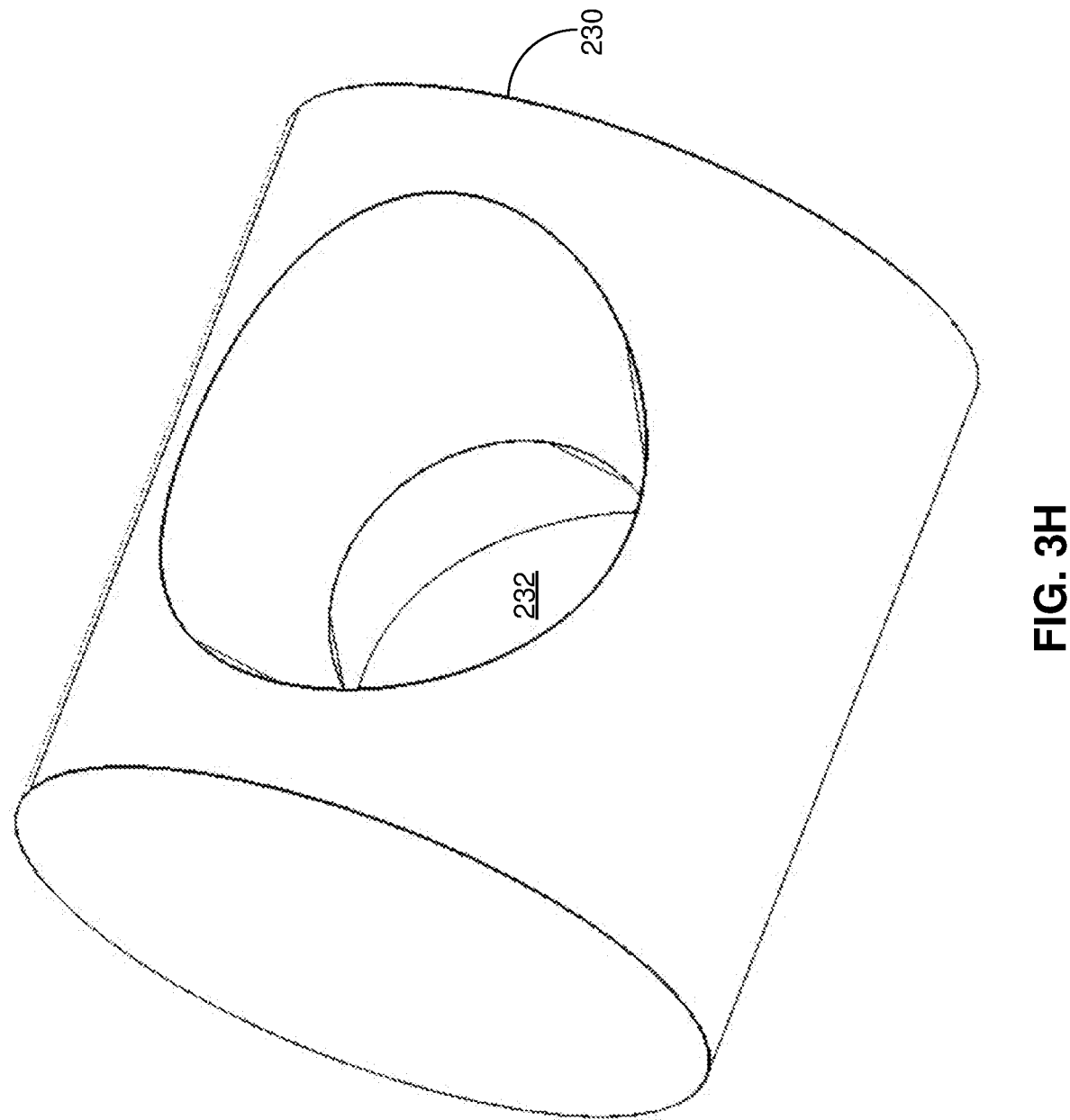
Figure 4B:
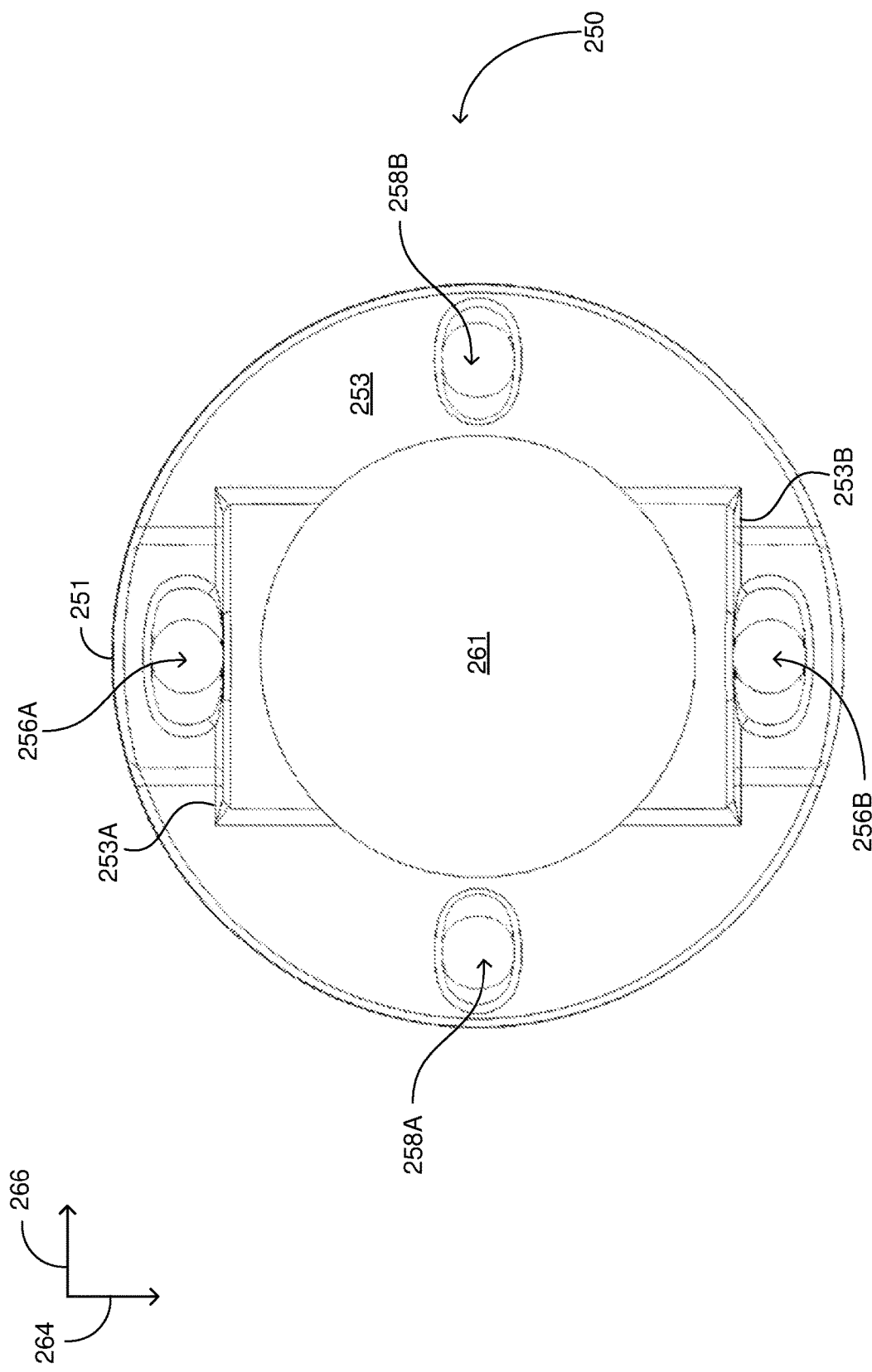
Figure 4C:
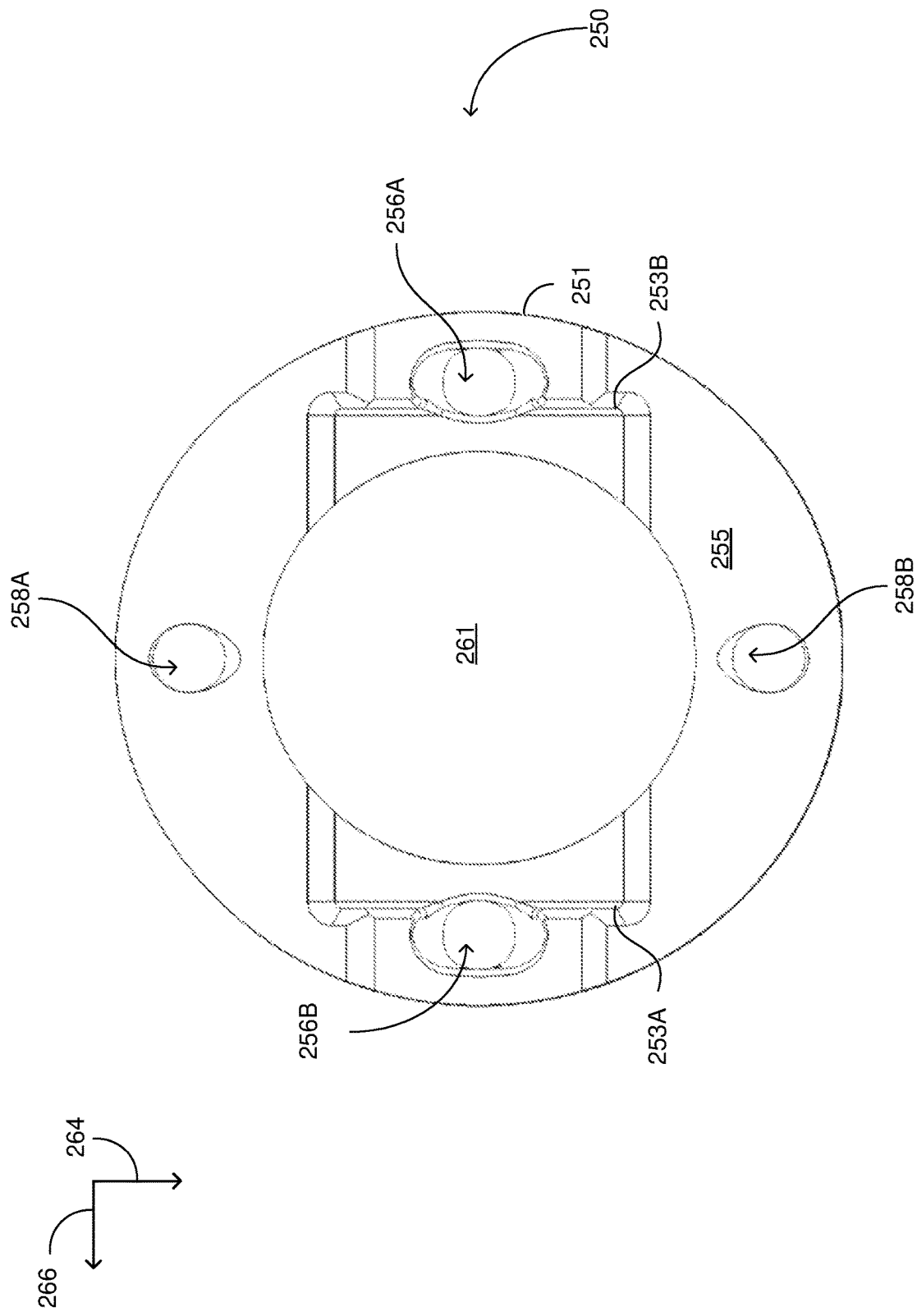
Figure 4D:
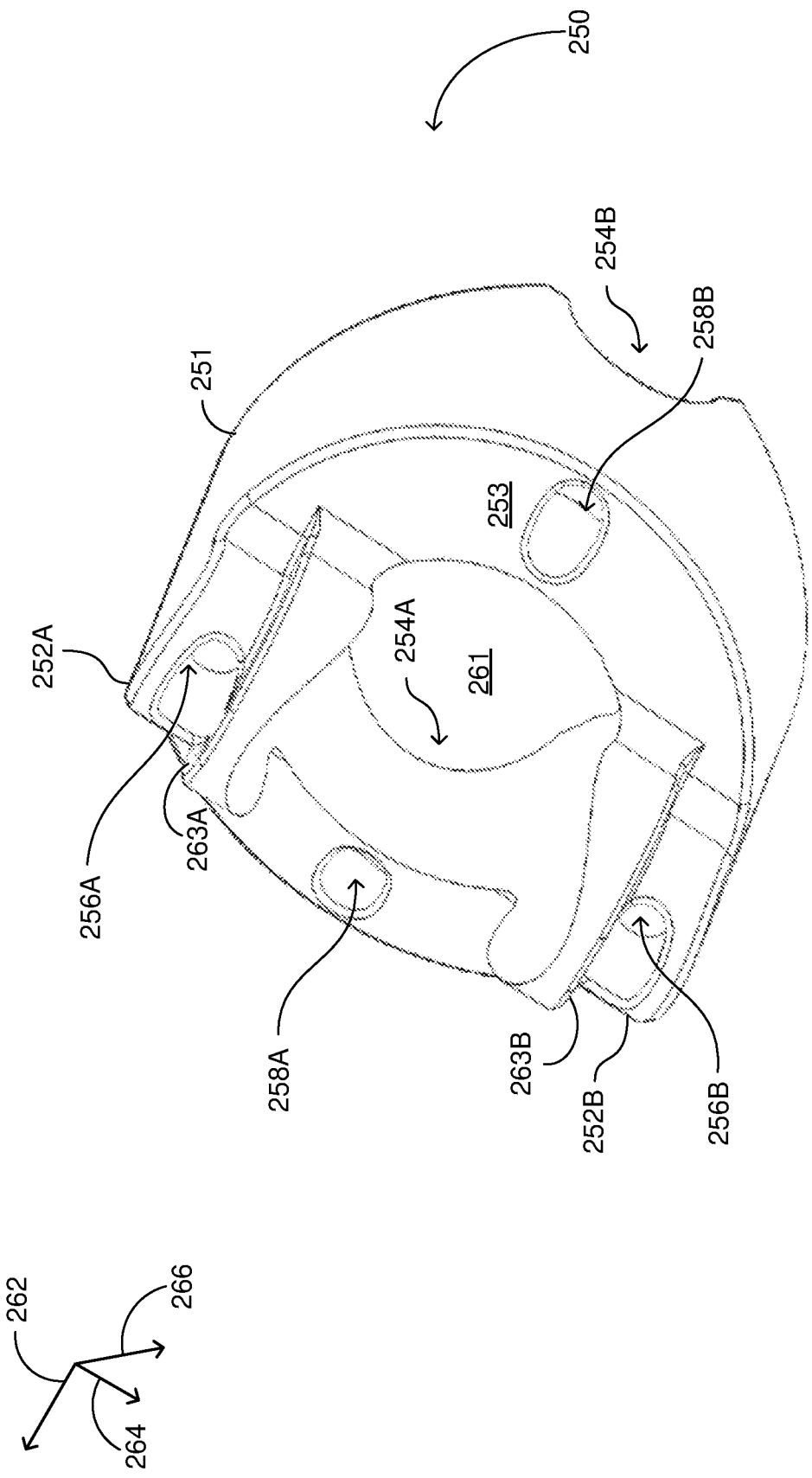
Figure 4E:
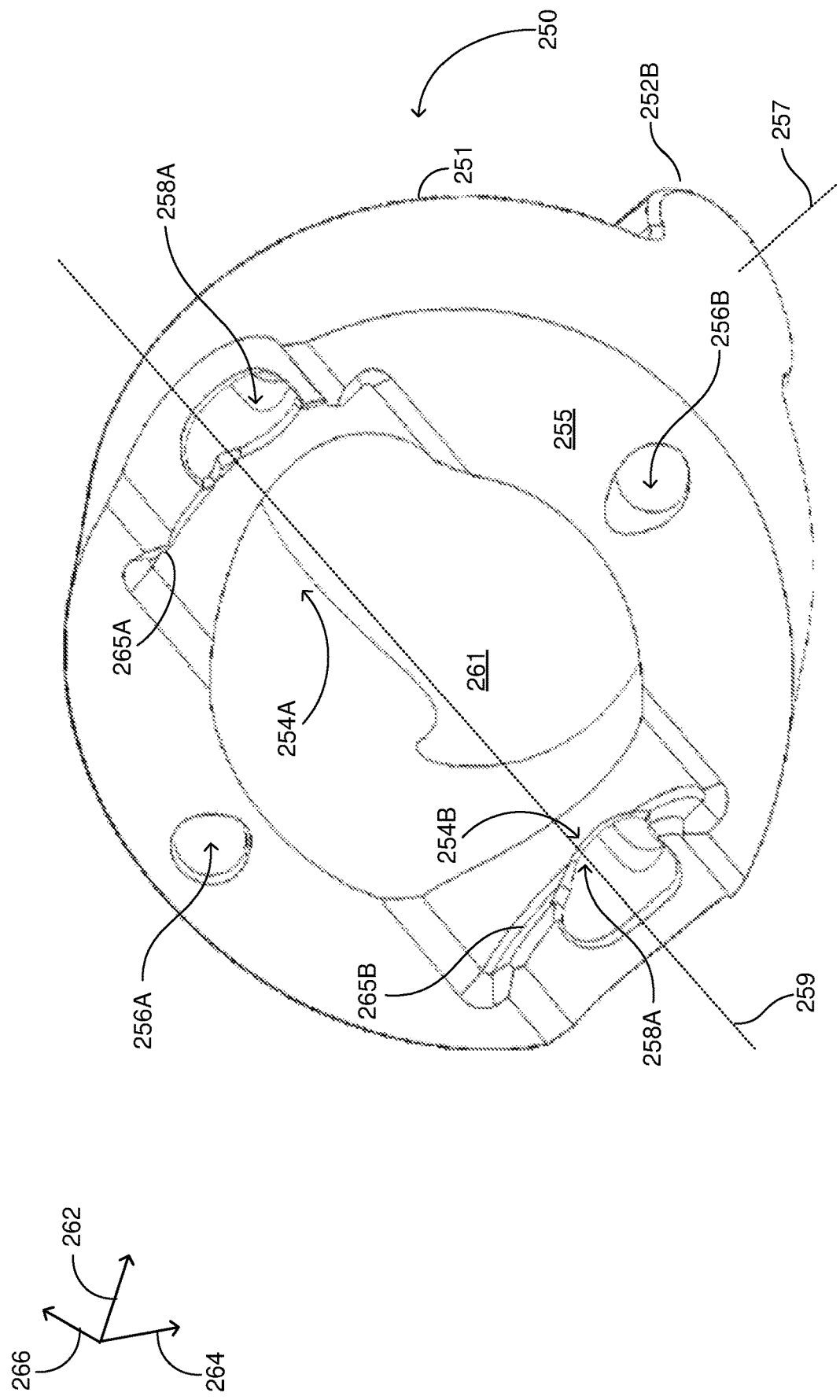

Reference is now made to FIGS. 3A-3H. FIGS. 3A-3F, are schematic illustrations of a link for an articulation arm, generally referenced 200, and FIGS. 3G and 3H are schematic illustration of pin, generally referenced 230 for connecting two links, both constructed and operative in accordance with a further embodiment of the disclosed technique. Link 200 includes a cylindrical vertebra 201, which includes two bases, a first base 203 and a second base 205. Two outer bearing portions 202A and 202B are formed on a radial line 207 of first base 203. In FIGS. 3A-3F, two outer bearing portions 202A and 202B are two outer axial shoulders 202A and 202B protruding from first base 203 of the cylinder. Two inner bearing portions 204A and 204B are formed on a radial line 209 of second base 205. Radial line 209 is perpendicular to radial line 207. In FIGS. 3A-3F, two inner bearing portions 204A and 204B are two inner axial shoulders 204A and 204B protruding from second base 205.

Link 200 includes four control bore holes 210A, 210B, 212A and 212B. Two of the control bore holes 210A and 210B enter second base 205 and exit a respective one of the outer bearing portions 202A and 202B. The other two of the control bore holes 212A and 212B enter first base 203 and exit a respective one of the inner bearing portions 204A and 204B.

Each one outer bearing portion 202A and 202B includes a respective pin hole 206A and 206B. Similarly each one of inner bearing portion 204A and 204B incudes a respective pin hole pin hole 208A and 208B. When two links are connected together, the pin holes of the outer axial shoulders of one link are aligned with the pin hole of the inner axial shoulders of the other link and connecting pins, such as connecting pin 230, are inserted through the aligned pin holes, thereby creating a bearing between two adjacent links such that the two adjacent links rotate one with respect to the other. For any three connected links, since axial outer shoulders and the axial inner shoulder are located on perpendicular radial lines, the axis of rotation between the first link and the second link is perpendicular to the axis of rotation between the second link and the third link. Also, connecting pin 230 includes a control bore hole 232. The connecting pin is inserted into the pin holes such that the control bore hole of the connecting pin is aligned with the control bore holes of the two links. Thus, the control bore holes pass through the bearings of the links. As mentioned above when the control bore holes pass through the bearings of the links, the area available for utility bore holes increases.

Reference is now made to FIGS. 4A-4E, which are schematic illustrations of a link for an articulation arm, generally referenced 250, constructed and operative in accordance with another embodiment of the disclosed technique. Link 250 includes a cylindrical vertebra 251 which includes two bases, a first base 253 and a second base 255. Two outer bearing portions 252A and 252B are formed on first base 253 and are located on a radial line 257 of first base 253. In FIGS. 4A-4E, two outer bearing portions 252A and 252B are two axial shoulders 252A and 252B protruding from one base of the cylinder. Two inner bearing portions 254A and 254B are formed in second base 255 and are located on a radial line 259 of second base 255. Radial line 259 is perpendicular to radial line 257. In FIGS. 4A-4E, two inner bearing portions 254A and 254B are two axial recesses 254A and 254B. Link 250 further includes and a central bore 261. Each of axial shoulders 252A and 252B includes a respective ledge 263A and 263B. Each of axial recesses 254A and 254B includes a respective ledge 265A and 265B. In link 250, the ledges 263A, 263B are located on the opposite side of the respective axial shoulder 252A and 252B, relative to ledges 113A and 113B of axial shoulders 102A and 102B of link 100 (FIGS. 1A-1E). Similarly ledges 265A and 265B are located on the opposite side of the respective axial recesses 254A and 254B, relative to ledges 115A and 115B of axial recesses 104A and 104B of link 100 (FIGS. 1A-1E).

Link 250 includes four control bore holes 256A, 256B, 258A and 258B. Two of the control bore holes 256A and 256B enter second base 255 and exit a respective one of the outer bearing portions 252A and 252B. The other two of the control bore holes 258A and 258B enter first base 253 and exit a respective one of the inner bearing portions 254A and 254B. Each of control bore holes 256A, 256B, 258A and 258B widens at the exits thereof to enable rotational motion of the link 250 when a control cable passes through control bore holes 256A, 256B, 258A and 258B. Link 250 may further include at least one utility bore holes similar to as described above.

Two links such as link 250 connect inserting the axial shoulders of one link to the axial recesses of the other link, thereby creating a bearing about which the two links rotate one with respect to the other. The ledges of the axial shoulders, such as ledges 253A and 253B are aligned with ledges 255A and 255B of the axial recesses, thereby preventing the two links from moving one with respect to the other in either one of the lateral directions 254 and 256

It will be appreciated by persons skilled in the art that the disclosed technique is not limited to what has been particularly shown and described hereinabove. Rather the scope of the disclosed technique is defined only by the claims, which follow.

The invention claimed is:

1. A link for an articulation arm comprising:
a vertebra, having a first base and a second base;
two outer axial shoulders, formed on said first base and located on a radial line of said first base and protruding from said first base, each of said two outer axial shoulders including a respective pin hole;
two inner axial shoulders, formed on said second base and located on a radial line of said second base and protruding from said second base, each of said two inner axial shoulders including a respective pin hole;
four control bore holes, two of said four control bore holes entering said second base and exiting a respective one of said outer axial shoulders and the other two of said control bore holes entering said first base and exiting a respective one of said inner axial shoulders;
two pins, each of said pins including a respective pin control bore hole,
wherein pin holes respective of said two outer axial shoulders are operable to be aligned with pin holes respective of two inner axial shoulders of another link and with respective pins, thereby enabling each of said pins to be inserted through two respective aligned pin holes, thereby creating a bearing between two adjacent links such that said two adjacent links rotate one with respect to the other, and
wherein said respective pin control bore hole of each said pins is aligned with a respective two control bore holes of each of said link and said another link.

2. The link according to claim 1, wherein each said control bore hole widens at the exits thereof.

3. The link according to claim 1, further including at least one utility bore hole, located between two adjacent ones of said control bore holes, said at least one utility bore hole passing through said link in the longitudinal direction thereof.

4. The link according to claim 1, wherein said two inner axial shoulders are axial recesses.

5. The link according to claim 4, wherein each of said outer axial shoulder and each of said axial recess includes a respective ledge.

6. An articulation arm including a plurality of links, each link including:
a vertebra, having a first base and a second base;
two outer axial shoulders, formed on said first base and located on a radial line of said first base and protruding from said first base, each of said two outer axial shoulders including a respective pin hole;
two inner axial shoulders, formed on said second base and located on a radial line of said second base and protruding from said second base, each of said two inner axial shoulders including a respective pin hole;
four control bore holes, two of said four control bore holes entering said second base and exiting a respective one of said outer axial shoulders and the other two of said control bore holes entering said first base and exiting a respective one of said inner axial shoulders;
two pins, each of said pins including a respective pin control bore hole,
wherein pin holes respective of said two outer axial shoulders are operable to be aligned with pin holes respective of two inner axial shoulders of another link and with respective pins, thereby enabling each of said pins to be inserted through two respective aligned pin holes, thereby creating a bearing between two adjacent links such that said two adjacent links rotate one with respect to the other, and
wherein said respective pin control bore hole of each said pins is aligned with a respective one of said two control bore holes of each of said link and said another link.

7. The articulation arm according to claim 6, wherein each said control bore hole widens at the exits thereof.

8. The articulation arm according to claim 6, wherein each of said link further includes at least one utility bore hole, located between two adjacent ones of said control bore holes, said at least one utility bore hole passing through said link in the longitudinal direction thereof.

9. The articulation arm according to claim 6, wherein said two inner axial shoulders are axial recesses.

10. The articulation arm according to claim 9, wherein each of said outer axial shoulder and each of said axial recess includes a respective ledge.

11. The articulation arm according to claim 10, wherein ledges of said axial shoulders of one link are aligned with ledges of the axial recesses of an adjacent link thereby prevent the two adjacent links from moving one with respect to the other in a lateral direction.

* * * * *